(12) United States Patent
Suri et al.

(10) Patent No.: US 10,080,522 B2
(45) Date of Patent: *Sep. 25, 2018

(54) CONNECTED DENTAL DEVICE

(71) Applicant: AT&T Intellectual Property I, L.P., Atlanta, GA (US)

(72) Inventors: Krishnapraveen Suri, San Ramon, CA (US); Perla Hizon, Pleasanton, CA (US)

(73) Assignee: AT&T Intellectual Property I, L.P., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/682,951

(22) Filed: Aug. 22, 2017

(65) Prior Publication Data

US 2017/0347953 A1 Dec. 7, 2017

Related U.S. Application Data

(63) Continuation of application No. 15/091,771, filed on Apr. 6, 2016, now Pat. No. 9,757,065.

(51) Int. Cl.
*A61C 17/22* (2006.01)
*A61B 5/00* (2006.01)
(Continued)

(52) U.S. Cl.
CPC .......... *A61B 5/4833* (2013.01); *A46B 5/0095* (2013.01); *A46B 15/0085* (2013.01);
(Continued)

(58) Field of Classification Search
None
See application file for complete search history.

(56) References Cited

U.S. PATENT DOCUMENTS

| 6,731,213 B1 | 5/2004 | Smith |
| 6,786,732 B2 | 9/2004 | Savill et al. |

(Continued)

FOREIGN PATENT DOCUMENTS

| CN | 102113762 | 7/2011 |
| WO | 2012108642 | 8/2012 |

(Continued)

*Primary Examiner* — Brent Swarthout
(74) *Attorney, Agent, or Firm* — Akerman LLP; Michael K. Dixon; Mammen (Roy) P. Zachariah, Jr.

(57) ABSTRACT

A system for providing a connected dental device is disclosed. In particular, the system may include integrating a network chip or transceiver into a dental device, such as a toothbrush, so as to enable the dental device to communicate with a user device and one or more accessory devices. Once the user device and one or more accessory devices are paired with the user device, the system may track information associated with the dental device and the user using the dental device. Based on the tracked information, the system may determine an action to be performed by the user using the dental device. Using the dental device, the system may transmit a notification to the user device to alert the user of the action that needs to be performed. The system may also transmit notifications providing status information for the dental device and the one or more accessory devices.

20 Claims, 4 Drawing Sheets

(51) Int. Cl.
  *A46B 15/00*  (2006.01)
  *A46B 5/00*  (2006.01)
  *A61B 1/00*  (2006.01)
  *A61B 1/04*  (2006.01)
  *A61B 1/24*  (2006.01)

(52) U.S. Cl.
  CPC ............ *A61B 1/00016* (2013.01); *A61B 1/04* (2013.01); *A61B 1/24* (2013.01); *A61B 5/0022* (2013.01); *A61B 5/4547* (2013.01); *A61B 5/486* (2013.01); *A61B 5/742* (2013.01)

(56) References Cited

U.S. PATENT DOCUMENTS

| | | |
|---|---|---|
| 8,585,411 B2 * | 11/2013 | Puurunen et al. ............ 434/263 |
| 8,717,852 B2 | 5/2014 | Cohen et al. |
| 8,758,022 B2 | 6/2014 | Kim |
| 8,918,940 B2 | 12/2014 | Gatzemeyer et al. |
| 9,027,192 B1 | 5/2015 | Cole |
| 9,072,370 B2 | 7/2015 | Gatzemeyer et al. |
| 9,757,065 B1 * | 9/2017 | Suri et al. ................ 340/539.12 |
| 2008/0146887 A1 | 6/2008 | Rao et al. |
| 2009/0215015 A1 | 8/2009 | Chu |
| 2009/0241278 A1 | 10/2009 | Lemchen |
| 2009/0262606 A1 * | 10/2009 | Trost ................................ 368/10 |
| 2010/0316975 A1 * | 12/2010 | Hilscher et al. .............. 433/216 |
| 2013/0000670 A1 | 1/2013 | Binner et al. |
| 2016/0143718 A1 | 5/2016 | Serval et al. |
| 2016/0235357 A1 | 8/2016 | Ohmer et al. |

FOREIGN PATENT DOCUMENTS

| | | |
|---|---|---|
| WO | 2014099593 | 6/2014 |
| WO | 2015073062 | 5/2015 |
| WO | 2014202250 | 12/2015 |

* cited by examiner

CONNECTED DENTAL DEVICE

CROSS-REFERENCE TO RELATED APPLICATION

This application is a continuation of and claims priority to U.S. patent application Ser. No. 15/091,771, now U.S. Pat. No. 9,757,065 filed on Apr. 6, 2016, which is herein incorporated by reference in its entirety.

FIELD OF THE INVENTION

The present application relates to technologies for oral care, dental devices, wireless devices, monitoring and alert systems, and communications networks, and more particularly, to a system and method for providing a connected dental device, such as a toothbrush.

BACKGROUND

In today's society, users are typically aware that practicing good oral hygiene habits are necessary in order to preserve oral health. For example, many users are aware that dentists typically recommend that users should brush their teeth after every meal, floss daily, and use a mouth rinse to kill bacteria, to prevent cavities, to prevent plaque buildup, to prevent gum disease, to prevent bad breath, or to prevent other oral-related conditions. Additionally, such users are typically aware that they should visit their dentist at least once a year for checkups and cleanings in order to maintain good oral health. In order to maintain their oral health, users typically utilize a variety of dental-related products. Such dental-related products include, but are not limited to, toothbrushes, toothpaste, oral irrigators, dental floss, water flossers, whitening strips, mouthwash, and other similar products. While users are often aware that they have to use such products in a certain manner in order to maintain good oral health, users often fail to do so. For example, instead of brushing their teeth with a toothbrush twice a day, many users may only brush their teeth once a day or at some other frequency. As another example, many users do not floss their teeth with dental floss on a regular basis, if at all. Similarly, many users do not brush their teeth in the correct manner for the correct duration of time recommended by dentists. Furthermore, many users fail to visit their dentist each year, and often only visit their dentist once an oral health issue has arisen.

While current oral health technologies provide a variety of beneficial features and functions, there is still room to substantially enhance and improve such technologies. For example, while current versions of electric toothbrushes provide substantially better cleaning action than standard non-electric toothbrushes, many users do not use electric toothbrushes correctly. Additionally, while many users have begun to use oral irrigators and water flossers in combination with traditional dental floss to remove plaque and bacteria buildup, such devices are often not used correctly or frequently enough. Based on the foregoing, oral health technologies may be modified so as to provide enhanced functionality for users, improved services for users, and additional features for users. Such enhancements and improvements to oral health technologies may provide for improved user satisfaction, improved user experiences, improved oral health, and increased user compliance with dentist-recommended regimens.

SUMMARY

A system and accompanying methods for providing a connected dental device are disclosed. In particular, the system and methods enable a dental device, such as a toothbrush, to be communicatively linked to a user device and a communications network so as to track and share information associated with a user's use of the dental device, generate and transmit various types of notifications, and facilitate the user in improving his or her oral health. In order to accomplish the foregoing, the system and methods may include incorporating a transceiver or other device (e.g. network chip) into a dental device so as to enable the dental device to communicate with the user device and the communications network. Additionally, a component of the dental device may include an identifier that may be utilized to identify a user that utilizes the dental device. For example, if the dental device is a toothbrush, a removable toothbrush head of the toothbrush may include a communications tag that contains information that identifies a particular user of the dental device. The communications tag may be scanned or otherwise accessed by the dental device, which may then provide the identifier and any other scanned information to an application of the user device.

The user may begin using the dental device to clean his or her teeth, and, while the user is using the dental device, sensors and components of the dental device may collect information associated with the user's use of the dental device. For example, a temperature sensor of the dental device may obtain temperature measurements for the dental device (or the user's mouth) and transmit the temperature measurements to the application of the user device. As another example, a camera of the dental device may record video content of the user's mouth and the dental device may transmit the video content to the application of the user device. Many types of additional information may be collected and transmitted to the application. For example, the dental device may collect information utilized to determine the angle at which the user holds the dental device while using the dental device, information utilized to determine the amount of pressure that the user presses the dental device against his or her teeth, information utilized to determine whether the user's mouth or gums are bleeding, information utilized to determine the user's blood sugar levels, information to determine the user's pattern of using the dental device, information to determine how long the user has utilized the dental device, information utilized to determine the user's brushing style, information utilized to determine power levels of the dental device, information utilized to determine an age of components of the dental device, along with any other information.

Based on the information collected, the system and methods may include analyzing the information to determine one or more actions that need to be performed using the dental device, by the user himself, or otherwise. For example, if the system determines that the user brushes the teeth on the right side of his mouth twice as long as the teeth on the left side of his mouth, the system may determine that the user needs to brush the teeth on the left side of his mouth for a longer duration. As another example, the system may determine that, based on the sensor information, that the user's gums are bleeding. In this case, the system may determine that the user needs to brush the areas of the user's teeth that are close to the user's gums more frequently. Once the action to be performed is determined, the system and methods may include transmitting a notification to the user device indicating the action to be performed. The notification may displayed on a graphical user interface of the application executing on the user device. The system and methods may then include determining if the action has been performed based on the user's subsequent use of the dental device. If the action has been performed, the system and methods may include transmitting a notification to the application indicating that the action has been successfully performed. If the action has not been performed, the system and methods may include transmitting a reminder notification to the application instructing the user to perform the action. In certain embodiments, the system and methods may also be utilized to schedule dentist appointments, provide reminders for upcoming dentist appointments, alert the user to recharge the dental device, alert the user to replace a component of the dental device, provide other alerts or reminders, or detect various dental conditions. As a result, the system and methods may assist users in maintaining oral health, maintaining compliance with regimens prescribed by dental professionals, and reducing incidences of dental or other diseases.

In one embodiment, a system for providing a connected dental device is disclosed. The system may include a memory that stores instructions and a processor that executes the instructions to perform various operations of the system. The system may perform an operation that includes communicatively pairing a dental device with a user device. In certain embodiments, the pairing may be facilitated via a wireless transceiver of the dental device. The system may then perform an operation that includes identifying, by utilizing the dental device, a first user associated with the dental device. The first user may be identified based on analyzing a first identifier of a first component of the dental device. The system may proceed to perform an operation that includes tracking, after identifying the first user and based on use of the dental device, information associated with the first user and the dental device. Based on the information associated with the first user and the dental device, the system may include performing an operation that includes generating a notification indicating an action to be performed with the dental device. Finally, the system may include performing an operation that includes transmitting the notification to the user device.

In another embodiment, a method for providing a connected dental device is disclosed. The method may include utilizing a memory that stores instructions, and a processor that executes the instructions to perform the various functions of the method. The method may include communicatively pairing a dental device with a user device. The pairing may be facilitated via a wireless transceiver of the dental device. Additionally, the method may include identifying, by utilizing the dental device, a first user associated with the dental device. The first user may be identified based on analyzing a first identifier of a first component of the dental device. After identifying the first user and based on use of the dental device, the method may include tracking information associated with the first user and the dental device. Based on the information associated with the first user and the dental device, the method may include determining an action to be performed with the dental device. The method may then include generating a notification indicating the action to be performed with the dental device. Finally, the method may include transmitting the first notification to the user device.

According to yet another embodiment, a computer-readable device having instructions for providing a connected dental device is provided. The computer instructions, which when loaded and executed by a processor, may cause the processor to perform operations including: communicatively pairing a dental device with a user device, wherein the pairing is facilitated via a wireless transceiver of the dental device; identifying, by utilizing the dental device, a first user associated with the dental device, wherein the first user is identified based on analyzing a first identifier of a first component of the dental device; monitoring, after identifying the first user and while the first user is using the dental device, information associated with the first user and the dental device; determining, based on the information associated with the first user and the dental device, an action to be performed with the dental device; generating a first notification indicating the action to be performed with the dental device; and transmitting the first notification to the user device.

These and other features of the systems and methods for providing a connected dental device are described in the following detailed description, drawings, and appended claims.

DETAILED DESCRIPTION OF THE INVENTION

Figure 1:
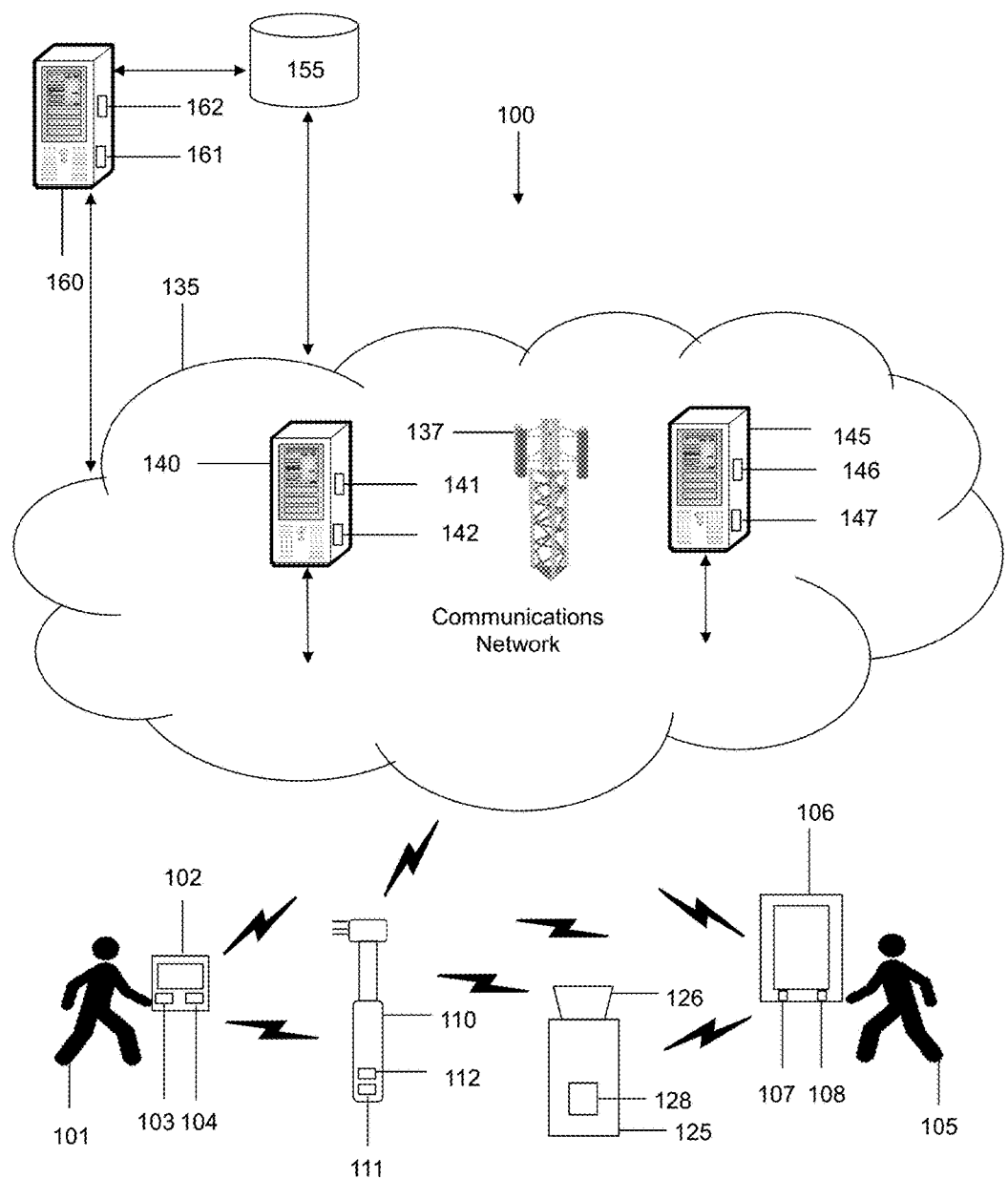
FIG. 1 is a schematic diagram of a system for providing a connected dental device according to an embodiment of the present disclosure.

A system 100 and accompanying methods for providing a connected dental device 110 are disclosed. In particular, the system 100 and methods enable a dental device 100, such as a toothbrush, to be communicatively linked to a user device (e.g. first user device 102) and a communications network 135 so as to track and share information associated with a user's use of the dental device 110, generate and transmit various types of notifications, and facilitate the user in improving his or her oral health. In order to accomplish the foregoing, the system 100 and methods may include incorporating a transceiver 117 or other device (e.g. network chip) into a dental device 110 so as to enable the dental device 110 to communicate with the user device and the communications network 135. Additionally, a component of the dental device may include an identifier that may be utilized to identify a user that utilizes the dental device. For example, if the dental device is a toothbrush, a removable toothbrush head 118 of the toothbrush may include a communications tag 119 that contains information that identifies a particular user of the dental device 110. The communications tag 119 may be scanned or otherwise accessed by the dental device 110, which may then provide the identifier and any other scanned information to an application of the user device.

The user may proceed to use the dental device 110 to clean his teeth, and sensors and components of the dental device 110 may collect information associated with the user's use of the dental device 110. For example, a temperature sensor 120 of the dental device 110 may obtain temperature measurements for the dental device 110 and transmit the temperature measurements to the application of the user device. As another example, cameras 122, 124 of the dental device 110 may record video content of the user's mouth and the dental device 110 may transmit the video content to the application of the user device. As a further example, an accelerometer 113 of the dental device 110 may indicate the speed at which the user moves the dental device 110, and a gyroscope 114 of the dental device may provide orientation information for the dental device 110. Many types of additional information may be collected and transmitted to the application. For example, the dental device may collect information utilized to determine the angle at which the user holds the dental device 110 while using the dental device 110, information utilized to determine the amount of pressure that the user presses the dental device 110 against his teeth, information utilized to determine whether the user's mouth or gums are bleeding, information utilized to determine the user's blood sugar levels, information to determine the user's pattern of using the dental device 110, information to determine how long the user has utilized the dental device 110, information utilized to determine the user's brushing style, information utilized to determine power levels of the dental device 110, information utilized to determine an age of components of the dental device 110, along with any other information. The system 100 and methods may also include obtaining information from one or more accessories associated with the dental device 110, such as a toothpaste dispenser 125, oral irrigator, water flosser, or other device.

Based on the information collected, the system 100 and methods may include analyzing the information to determine one or more actions that need to be performed using the dental device 110, by the user himself, or otherwise. For example, if the system 100 determines that the user has utilized a toothbrush head 118 of the dental device 110 for greater than a threshold period of time, the system 100 may determine that the user needs to replace the toothbrush head 118. As another example, the system 100 may determine that, based on the sensor information, that the user has a cavity in one of his teeth. In this case, the system 100 may determine that the user needs to go to the dentist within a certain period of time. Once the action to be performed is determined, the system 100 and methods may include transmitting a notification to the user device indicating the action to be performed. The notification may displayed on a graphical user interface of the application executing on the user device. The system 100 and methods may then include determining if the action has been performed based on the user's subsequent use of the dental device, based on the user inputting information indicating completion of the action, or by receiving information from the user's dental professional. If the action has been performed, the system 100 and methods may include transmitting a notification to the application indicating that the action has been successfully performed. If the action has not been performed, the system 100 and methods may include transmitting a reminder notification to the application, which reinstructs the user to perform the action. In certain embodiments, the system 100 and methods may also be utilized to schedule dentist appointments, provide reminders for upcoming dentist appointments, alert the user to recharge the dental device 110, alert the user to replace a component of the dental device, provide other alerts or reminders, or detect various dental conditions. As a result, the system 100 and methods may assist users in maintaining oral health, maintaining compliance with regimens prescribed by dental professionals, and reducing incidences of dental or other diseases.

As shown in FIG. 1, a system 100 that provides a connected dental device is disclosed. The system 100 may be configured to support, but is not limited to supporting, cloud computing services, dental applications and services, content delivery services, IPTV services, IP Multimedia Subsystem (IMS) services, satellite services, fiber services, telephone services, voice-over-internet protocol services (VoIP), voice-over-long-term-evolution (VoLTE) services, LTE services, software as a service (SaaS) applications, healthcare applications and services, gaming applications and services, social media applications and services, operations management applications and services, productivity applications and services, mobile applications and services, and any other computing applications and services. The system may include a first user 101 that may utilize a first user device 102 to access content, data, and services, or to perform a variety of other functions. As an example, the first user 101 may utilize first user device 102 to transmit signals to the system 100 to request various types of media content stored within the database 155, perform any other operations, or any combination thereof. Media content may include, but is not limited to, audio content, video content, image content, web content, text content, any type of content, or any combination thereof. As another example, the first user 101 may utilize the first user device 102 to communicatively interact with the dental device 110, the dispenser 125, any other device in the system 100, or any combination thereof.

In certain embodiments, the first user 101 may be a subscriber of a service provider that controls communications network 135, and the first user device 102 may be equipped for mobile communication. The first user device 102 may include a memory 103 that includes instructions, and a processor 104 that executes the instructions from the memory 103 to perform the various operations that are performed by the first user device 102. In certain embodiments, the processor 104 may be hardware, software, or a combination thereof. In certain embodiments, the first user device 102 may be a computer, a laptop, a set-top-box, a tablet device, a phablet, a server, a mobile device, a smartphone, a smart watch, or any other type of computing device. Illustratively, the first user device 102 is shown as a smartphone device in FIG. 1. In certain embodiments, the first user device 102 may communicate with the other devices in the system 100 by utilizing infrared radiation, Bluetooth connectivity, ZigBee, Z-Wave, any type of wireless protocol, radio technologies, or any combination thereof. In certain embodiments, the first user device 102 may include a wireless transceiver, module, and/or chip, such as a Bluetooth chip, near-field communications chip, or other similar technology to enable the first user device 102 to communicate with other devices in the system 100.

The system may also include a second user 105 that may utilize a second user device 106 to also access content, data, and services, and to perform a variety of other functions. For example, the second user device 106 may be utilized by the second user 105 to transmit signals to request various types of content, services, and data provided by content and service providers associated with the communications network 135 or any other network in the system 100. In certain embodiments, the second user 105 may be a subscriber of a service provider that controls communications network 135. The second user device 106 may be equipped for mobile communication. The second user device 106 may include a memory 107 that includes instructions, and a processor 108 that executes the instructions from the memory 107 to perform the various operations that are performed by the second user device 106. In certain embodiments, the processor 108 may be hardware, software, or a combination thereof. Similar to the first user device 102, in certain embodiments, the second user device 106 may be a computer, a laptop, a tablet device, a phablet, a server, a mobile device, a smartphone, a smart watch, or any other type of computing device. Illustratively, the second user device 106 is shown as a tablet device in FIG. 1. In certain embodiments, the second user device 106 may communicate with the other devices in the system 100 by utilizing infrared radiation, Bluetooth connectivity, ZigBee, Z-Wave, any type of wireless protocol, radio technologies, or any combination thereof. In certain embodiments, the second user device 106 may include a wireless transceiver, module, and/or chip, such as a Bluetooth chip, near-field communications chip, or other similar technology to enable the second user device 106 to communicate with other devices in the system 100.

In certain embodiments, the first and second devices 102, 106 may have any number of software applications and/or application services stored and/or accessible thereon. For example, the first and second devices 102, 106 may include healthcare applications, cloud-based applications, VoIP applications, other types of phone-based applications, product-ordering applications, business applications, e-commerce applications, media streaming applications, content-based applications, media-editing applications, database applications, gaming applications, internet-based applications, browser applications, mobile applications, service-based applications, productivity applications, video applications, music applications, social media applications, any other type of applications, any types of application services, or a combination thereof. In certain embodiments, the software applications and services may include one or more graphical user interfaces so as to enable the first and second users 101, 105 to readily interact with the software applications. The software applications and services may also be utilized by the first and second users 101, 105 to interact with any device in the system 100, any network in the system 100, or any combination thereof. In certain embodiments, the first and second devices 102, 106 may include associated telephone numbers, device identities, or any other identifiers to uniquely identify the first and second devices 102, 106.

In certain embodiments, the first and second devices 102, 106 may have corresponding device profiles. In certain embodiments, each of the other devices in the system 100 may have their own corresponding device profiles. For example, the dental device 110 and the dispenser 125 of system 100 may have their own device profiles. Information included in a device profile may include, but is not limited to, information specifically corresponding to the first and second devices 102, 106, information identifying the types of devices that the first and second devices 102, 106 are, information relating to how the first user 101 utilizes the first user device 102, information relating to how the second user 105 utilizes the second user device 106, information identifying what type of services and information the first user 101 and second user 105 access, information indicating each type of component included in the first and second devices 102, 106, information identifying the processing power, storage capacity, download capabilities, and upload capabilities associated with the first and second devices 102, 106, any other information associated with the first and second devices 102, 106, or any combination thereof. The device profiles may be made accessible to any device, network, or a combination thereof, in the system 100.

In addition to device profiles, the system 100 may also include user profiles. A user profile may be a profile corresponding to the first user 101, the second user 105, or any other user. For example, the first user's 101 profile may include information, such as, but not limited to, a name of the first user 101, the age of the first user 101, demographic information associated with the first user 101, information identifying the first user device 102 of the first user 101, the types of services, such as content delivery services, subscribed to by the first user 101, information identifying a location of the first user 101, information identifying the applications that the first user 101 utilizes, information that identifies the first user's 101 toothbrush head 118, information that identifies how the first user 101 utilizes the dental device 110, information obtained from any of the sensors of the dental device 110, information associated with the dispenser 125, any information collected in the system 100, and any other information. The user profiles may be stored directly on the first user device 102, the second user device 106, the database 155, on any other device in the system 100, or on any combination thereof. Additionally, the user profiles may be accessible by any device in the system 100, any network in the system 100, or a combination thereof.

Figure 2:
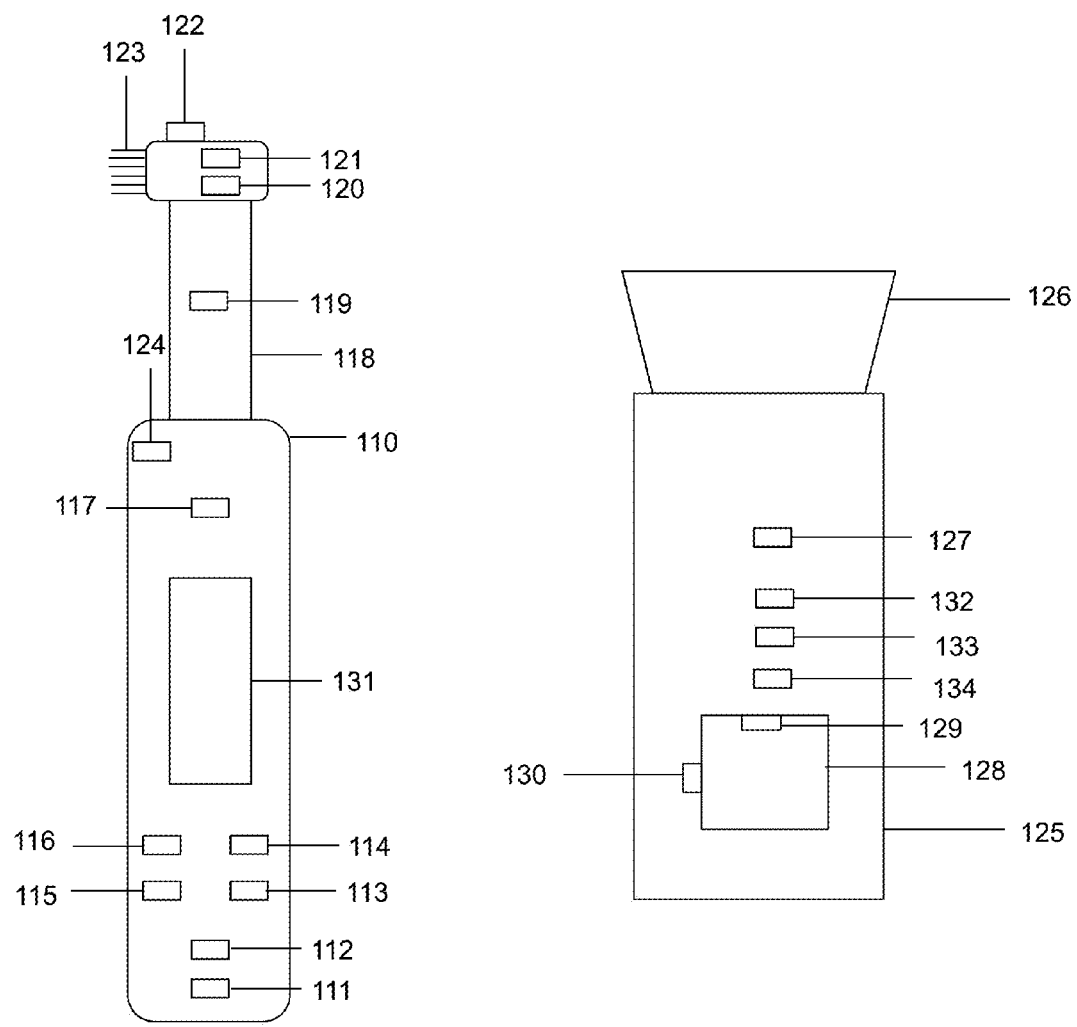
FIG. 2 is a schematic diagram illustrating various components of the connected dental device and various components of the dispenser utilized in the system of FIG. 1.

The system 100 may include a dental device 110 that may be utilized by the first and second users 101, 105. The dental device 110 may be any type of dental device including, but not limited to, an electric toothbrush, a traditional toothbrush, an oral irrigator, a water flosser, a teeth whitener device, a retainer, a mouthpiece, a dental pick, a gingival stimulator, a dental scraper, a dental explorer, any type of dental instrument, or any combination thereof. In FIGS. 1-2, the dental device 110 is illustratively shown as an electric toothbrush. In certain embodiments, the dental device 110 may include a memory 111 that stores instructions and a processor 112 that executes the instructions to perform various operations performed by the dental device 110. In certain embodiments, the processor 112 may be hardware, software, or a combination thereof. The memory 111 may be configured to store any information about the dental device 110, such as, but not limited to, information identifying the model of the dental device 110, technical specifications of the dental device 110, how and when the dental device 110 is activated and/or used, any other information associated with the dental device 110, an identification of users that use the dental device 110, any other information, or any combination thereof. The dental device 110 may include one or more sensors and/or components. For example, the dental device 110 may include an accelerometer 113, which may be configured to measure a rate of acceleration associated with movements made by the dental device 110. In certain embodiments, the accelerometer 113 may be configured to measure the rate at which the dental device 110 vibrates when switched on and used by a user, such as the first user 101.

In certain embodiments, the dental device 110 may also include a gyroscope 114, which may be configured to measure the orientation of the dental device 110 and how the dental device 110 is rotated during use. Additionally the gyroscope 114 may collect measurements that may be utilized to determine the angles at which the dental device 110 is held by a user while using the dental device 110 or otherwise. The dental device 110 may also include a compass 115, which may be utilized to determine a direction in which the dental device is facing. For example, the compass 115 may be utilized to determine where the direction at which the toothbrush head 118 of the dental device 110 is facing. The dental device 110 may also include a power source 116, which may be a rechargeable battery or other power source that may deliver power to the dental device 110 to allow it to operate. In certain embodiments, the dental device 110 may include a transceiver 117, which may include any functionality and componentry of a transceiver and may include an antenna, which may be utilized to transmit and receive signals to communicate with the various devices in the system 100, such as, but not limited to, first user device 102, second user device 106, dispenser 125, servers 140, 145, cell site 137, or any combination thereof. In certain embodiments, the transceiver 117 may enable the dental device 110 to communicate using various types of wireless technologies, such as, but not limited to radio frequency identification (RFID), NFC, Bluetooth, Bluetooth Low Energy, Zigbee, Z-Wave, and other such technologies.

In certain embodiments, the dental device 110 may include a camera 124, which may be configured to record media content. For example, when a user is using the dental device 110, the camera 124 may be utilized to record video content of the user's mouth as the user is brushing his teeth. The dental device 110 may also include a display 131, which may be a liquid crystal display (LCD) or other type of display. The display 131 may be configured to display status updates associated with the dental device 110, notifications generated by the system 100, information associated with the first and second users 101, 105, any other information, or any combination thereof. Additionally, the dental device 110 may include any number of sensors, such as, but not limited to, a temperature sensor, a pressure sensor, a pH sensor, a blood sugar sensor, any other type of sensor, or any combination thereof. The sensors may be located within the dental device 110, on an external surface of the dental device 110, or at any other desired location. Information gathered and/or received by the accelerometer 113, gyroscope 114, compass 115, transceiver 117, the camera 124, or any combination thereof, may be transmitted to any device in the system 100, such as for further processing.

The dental device 110 may further include a toothbrush head 118, which may be configured to be removable. In certain embodiments, the first user 101 may have his own toothbrush head 118 and the second user 105 may also have his own toothbrush head 118. Each toothbrush head 118 may include a communications tag 119, such as a RFID tag, NFC tag, other tag, or any combination thereof. In certain embodiments, the communications tag 119 may be a passive communications tag, which may receive energy from a radio frequency field generated by the transceiver 117 antenna in order to activate. In certain embodiments, the communications tag 119 may be an active communications tag, which may have its own power source and transceiver/antenna to allow it to communicatively pair with the dental device 110 without requiring the energy emitted by the transceiver 117 of the dental device 110. The communications tag 119 may store one or more identifiers associated with the user that uses the toothbrush head 118. For example, if the first user's 101 name is John Smith, the identifier in the communications tag 119 may indicate his name, a hash of his name, or any other identifier that may be utilized to identify the first user 101. The communications tag 119 may also store information relating to a particular user's dental habits, such as, but not limited to, when the user brushes his teeth, how long the user brushes his teeth, the brushing style that the user uses when brushing his teeth, usage patterns for using the dental device 110, demographic information for the user, sensor measurements obtained from sensors of the dental device 110 and/or toothbrush head 118, dental and/or medical record information for a user, any other information, or any combination thereof.

When the toothbrush head 118 is attached to the dental device 110, the dental device 110 may communicatively pair with the communications tag 119 in the toothbrush head 118. The dental device 110 may accomplish this by utilizing the transceiver 117, which may emit a radio frequency field or signal that may activate the communications tag 119 in the toothbrush head 118. Upon activation, the communications tag 119 may transmit any information stored therein to the transceiver 117 of the dental device 110, which may then forward the information to the first and second user devices 102, 106, and/or to the communications network 135, or to any other device. In certain embodiments, the information obtained from the communications tag 119 may be stored in the memory 111 of the dental device 110. The information obtained from the communications tag 119 may be utilized to identify the user that is using the dental device 110. When the user removes the toothbrush head 118 and a different user attaches a different toothbrush head 118 to the dental device 110, the information stored in the communications tag 119 of the different toothbrush head 118 may be utilized to identify the different user that is using the dental device. In certain embodiments, instead of using the communications tag 119, the toothbrush head 118 may include a quick response (QR) code, barcode, or other scannable code which may be read by the dental device and/or first and second user devices 102, 106. The codes may include the same or similar information that may be included on the communications tag 119.

In certain embodiments, the toothbrush head 118 may include one or more sensors. For example, the toothbrush head 118 may include a temperature sensor 120, which may be configured to measure the temperature of the dental device 110 and/or the toothbrush head 118. The temperature sensor 120 is illustratively shown as being on the head of the toothbrush head 118 in FIG. 2, however, the temperature sensor 120 may be positioned at any other suitable location on the dental device 110. The toothbrush head 118 may also include a sensor 121, which may be configured to monitor the user's blood sugar levels, glucose levels, pH levels, plaque levels, bacteria levels, heart rate, or any other biologically-related metrics, such as when the user is using the dental device 110. The toothbrush head 118 may also include a camera 122, which may be similar to camera 124. In certain embodiments, the camera 122 may be configured to record media content. For example, when a user is using the dental device 110, the camera 122 may be utilized to record video content of the user's mouth while the user is brushing his teeth. The toothbrush head 118 my further include a plurality of bristles 123, which the user may use to brush his teeth. In certain embodiments, by using the camera 122 and/or the sensor 121, the age and/or wear of the bristles 123 may be determined. Information indicating the age and/or wear of the bristles 123 may be utilized by the system 100 to determine whether the toothbrush head 118 needs to be replaced.

In certain embodiments, the system 100 may include a dispenser 125, which may be configured to dispense toothpaste, mouthwash, teeth whitening fluid, any other dental solution or cleaning agent, or any combination thereof. The dispenser 125 may be configured to receive a portion of a container 126 that contains toothpaste or other dental solutions or cleaning agents. The dispenser 125 may include a chip or transceiver 127, which may include any functionality and componentry of a transceiver and may include an antenna, which may be utilized to transmit and receive signals to communicate with the various devices in the system 100, such as, but not limited to, first user device 102, second user device 106, dental device 110, servers 140, 145, cell site 137, the toothbrush head 118, or any combination thereof. In certain embodiments, the transceiver 127 may enable the dispenser 125 to communicate using various types of wireless technologies, such as, but not limited to RFID, NFC, Bluetooth, Bluetooth Low Energy, Zigbee, Z-Wave, and other such technologies. The transceiver 127 may allow the dispenser 125 to pair with the dental device 110, the first and second user devices 102, 106, the toothbrush head 118, any other device in the system 100, or any combination thereof. The transceiver 127 may also allow any information stored in the components of the dispenser 125 to be transmitted to any of the devices in the system 100.

The dispenser 125 may also include an area 128 in which the user may place the head of the toothbrush head 118 so as to receive toothpaste or another cleaning agent from the dispenser 125. In certain embodiments, instead of placing the head of the toothbrush head 118 in the area 128, the user may place a cup or other receptacle in the area 128 so as to receive the toothpaste or other cleaning agent housed in the container 126. When the head of the toothbrush head 118 or the cup is placed in the area 128, a sensor 130 (e.g. infrared sensor or other sensor) may detect the presence of the head or the cup and cause the toothpaste or other cleaning agent to be dispensed via the opening 129 onto the head of the toothbrush head 118 or into the cup that has been positioned in the area 128. In certain embodiments, the dispenser 125 may include a memory 132 that stores instructions and a processor 133 that executes the instructions to perform various operations performed by the dispenser 125. In certain embodiments, the processor 133 may be hardware, software, or a combination thereof. The memory 132 may be configured to store any information about the dispenser 125, such as, but not limited to, information identifying the model of the dispenser 125, information identifying the types of toothpaste and/or cleaning agents that may be dispensed from the dispenser 125, technical specifications of the dispenser 125, how and when the dispenser 125 is activated and/or used, any other information associated with the dental device 110, an identification of users that use the dispenser 125, any other information, or any combination thereof. The dispenser 125 may also include a power source 134, which may be configured to power the components of the dispenser 125. In certain embodiments, radio frequency fields emitted by the transceiver 117 antenna of the dental device 110 may be utilized to power the dispenser 125, such as if the dispenser 125 includes a RFID tag and/or NFC tag.

The system 100 may also include a communications network 135. The communications network 135 of the system 100 may be configured to link each of the devices in the system 100 to one another. For example, the communications network 135 may be utilized by the first user device 102 to connect with other devices within or outside communications network 135, such as, but not limited to, dental device 110, dispenser 125, servers 140, 145, toothbrush head 118, database 155, or any combination thereof. Additionally, the communications network 135 may be configured to transmit, generate, and receive any information and data traversing the system 100. In certain embodiments, the communications network 135 may include any number of servers, databases, or other componentry, and may be controlled by a service provider. In certain embodiments, the communications network 135 may be subscribed to by the first and second users 101, 105. The communications network 135 may also include and be connected to a radio access network, a cloud-computing network, an IMS network, a VoIP network, a VoLTE network, an LTE network, a wireless network, an Ethernet network, a fiber network, a satellite network, a broadband network, a cellular network, a private network, a cable network, the Internet, an internet protocol network, a multiprotocol label switching (MPLS) network, a content distribution network, an internet protocol television network, a short-range wireless network any network, or any combination thereof. Illustratively, servers 140, 145 are shown as being included within communications network 135. In certain embodiments, the communications network 135 may be part of a single autonomous system that is located in a particular geographic region, or be part of multiple autonomous systems that span several geographic regions.

In certain embodiments, the communications network 135 may be configured to deliver content and services using an internet protocol suite and by utilizing packet switching. The communications network 135 may provide the ability to stream information and media requested by the first and second users 101, 105, the dispenser 125, and/or the dental device 110, provide for media-on-demand, provide any type of content, provide any type of information, or any combination thereof. The communications network 135 may include one or more cell sites 137 that may be utilized to communicate with the first user device 102, the second user device 106, the dental device 110, the toothbrush head 118, the dispenser 125, the server 160, any other device, or any combination thereof. In certain embodiments, the cell site 137 may include hardware components that include any of the functional features of a radio access network. The cell site 137 may be configured to provide cellular services (e.g. LTE services), wireless services, any type of services, or any combination thereof. Additionally, the cell site 137 may include any of the functionality of a base station utilized in mobile communication networks. For example, the cell site 137 may include any number of antennae, transceivers, digital signal processors, control electronics, GPS receivers, electrical power sources, radio equipment, and electronics equipment to create a cell for the communications network 135. The cell site 137 may be configured to communicate with and receive content and data streams from any other network, from any device in the system 100, or any combination thereof.

Notably, the functionality of the system 100 may be supported and executed by using any combination of the servers 140, 145, and 160. In certain embodiments, the servers 140, 145, and 160 may be content delivery servers and may include any functionality associated with content delivery servers. In certain embodiments, the server 140 may include a memory 141 that includes instructions, and a processor 142 that executes the instructions from the memory 141 to perform various operations that are performed by the server 140. The processor 142 may be hardware, software, or a combination thereof. Similarly, the server 145 may include a memory 146 that includes instructions, and a processor 147 that executes the instructions from the memory 146 to perform the various operations that are performed by the server 145. In certain embodiments, the servers 140, 145, and 160 may be network servers, routers, gateways, computers, mobile devices or any other suitable computing device. In certain embodiments, the servers 140, 145 may be communicatively linked to the communications network 135, any network, any device in the system 100, or any combination thereof.

The database 155 of the system 100 may be utilized to store and relay information that traverses the system 100, cache content that traverses the system 100, store data about each of the devices in the system 100 and perform any other typical functions of a database. In certain embodiments, the database 155 may be connected to or reside within the communications network 135, any other network, or a combination thereof. Additionally, the database 155, in certain embodiments, may serve as a content source for stored content that may be accessed by the communication network 135 so that the communication network 135 may obtain content for the first and second users 101, 105 in an efficient and effective manner. In certain embodiments, the database 155 may serve as a central repository for content and information requested by the first and second users 101, 105 and/or other devices in the system 100. Furthermore, the database 155 may include a processor and memory or be connected to a processor and memory to perform the various operation associated with the database 155.

In certain embodiments, the database 155 may be connected to the servers 140, 145, 160, the cell site 137, first user device 102, second user device 106, the dental device 110, the dispenser 125, the toothbrush head 118, or any combination thereof. The database 155 may also store information and metadata obtained from the system 100, store media content; store metadata and other information associated with the first and second users 101, 105; store user profiles associated with the first and second users 101, 105; store device profiles associated with the first user device 102, the second user device 106, the dental device 110, the toothbrush head 118, the dispenser 125, and/or other device in the system 100; store location information; store communications traversing the system 100; store user preferences; store information associated with any device or signal in the system 100; store information relating to patterns of usage relating to any of the devices in the system 100; store content; store information utilized for identifying communications network 135; store network condition information; store lists identifying all devices associated with a particular user; store appointment information (e.g. dental appointments) for the first and second users 101, 105; store information collected from any of the sensors and/or camera 124 of the dental device 110; store information collected from any of the sensors and/or camera 122 of the toothbrush head 118; store any dental information for the first and second users 101, 105; store information identifying actions to be performed with the dental device 110; store information identifying whether the actions have been performed; store information generated by or associated with the dental device 110, the dispenser 125, the first user device 102, the second user device 106, and/or the toothbrush head 118; store any information traversing the system 100; store any information generated by the system 100, or any combination thereof. Furthermore, the database 155 may be configured to process queries sent to it by any device in the system 100.

Operatively, the system 100 may provide a connected dental device 110, as shown in the following exemplary scenario. In the example scenario, the first user 101 may be a person that is getting ready to go to work and is about to brush his teeth. While approaching his bathroom, the first user 101 may bring the first user device 102 (e.g. smartphone) within pairing range of the dental device 110 and/or the dispenser 125. For this example, the pairing range may mean the distance between the first user device 102 and the dental device 110 and/or dispenser 125 that effectively allows the dental device 110 and/or dispenser 125 to be within communication range of the first user device 102. Once within pairing range, the first user device 102 may be paired, such as via Bluetooth, NFC, or other wireless technologies, with the dental device 110 and/or dispenser 125. Once paired, the dental device 110 may transmit any information associated with and/or stored on the dental device 110 to the first user device 102, and the dispenser 125 may transmit any information associated with and/or stored on the dispenser 125 to the first user device 102. Such information may include, but is not limited to, a power level of the dental device 110, information identifying when the dental device 110 was last used and for how long, historical information pertaining to the use of the dental device 110, a power level of the dispenser 125, information identifying when the dispenser 125 was last used and how often the dispenser 125 has been used, historical information pertaining to the use of the dispenser 125, along with any other information.

The first user 101 may proceed to attach his personal toothbrush head 118 to the dental device 110, and the dental device 110 may pair with the toothbrush head 118 and obtain any information contained in the communications tag 119 of the toothbrush head 118 by utilizing the transceiver 117. In certain embodiments, the dental device 110 may obtain the information from a QR code, barcode, magnetic strip, or other readable medium of the toothbrush head 118. The obtained information may indicate the name of the first user 101, the first user's 101 brushing or dental habits, when the first user 101 last used the toothbrush head 118 with the dental device 110, any information associated with use of the dental device 110 and/or dispenser 125, any other information associated with the first user 101, or any combination thereof. Once the toothbrush head 118 is attached and paired to the dental device 110, the system 100 may track information associated with the first user 101, the dental device 110, the dispenser 125, and/or the toothbrush head 118. In certain embodiments, the information may be tracked once the first user 101 activates the dental device 110 and while the first user 101 is using the dental device 110 to brush his teeth. The information that may be tracked may include, but is not limited to, any information obtained from any of the sensors of the dental device 110 and/or toothbrush head 118 (e.g. blood sugar levels, pH levels, temperature measurements, etc.), any calculations performed by the dental device 110, any information obtained from the dispenser 125, any media content from the cameras 122, 124, any other information, or any combination thereof. Additional information that may be tracked may include the angle at which the first user 101 holds the dental device 110 while using the dental device 110, the brushing speed mode selected by the first user 101 (e.g. modes associated with how fast the bristles 123 vibrate or move), the brushing technique that the first user 101 uses while using the dental device 110, the pressure at which the first user 101 holds the toothbrush head 118 against his teeth (e.g. by using a pressure sensor of the dental device 110), the duration of time that the first user 101 uses the dental device 110, the times of day that the first user 101 activates and/or uses the dental device 110, how often the first user 101 uses the dispenser 125 to dispense toothpaste or other cleaning agents, power levels of the dental device 110 and/or the dispenser 125, any other information, or a combination thereof. The tracked information may be sent to any device or network in the system 100.

Based on the tracked information, the system 100 may determine one or more actions to be performed by the first user 101 with the dental device 110, one or more actions to be performed by the first user 101 with the dispenser 125, one or more actions to be performed with the toothbrush head 118, one or more other actions to be performed by the first user 101, or any combination thereof. For example, based on media content received from the cameras 122, 124, the system 100 may determine that the first user 101 has plaque buildup in between several of his teeth. In this case, the system 100 may determine that the first user 101 needs to use an oral irrigator, water flosser, or traditional dental floss in addition to using the dental device 110. As another example, based on the tracked information obtained from the sensors of the toothbrush head 118, the dental device 110, and/or the dispenser 125, the system 100 may determine that the first user 101 did not brush his teeth for the duration recommended by his dentist. In this case, the system 100 may determine that the first user 101 needs to continue using the dental device 110 for additional time until the recommended duration is reached. The system 100 may then proceed to generate and transmit a notification or alert indicating the action to be performed. For example, either the dental device 110, the servers 140, 145, or a combination thereof, may transmit the notification indicating the action to be performed to the first user device 102. An application of the first user device 102 may display the notification via a graphical user interface of the application, cause the notification to be outputted as a sound (e.g. speech or other sound), cause a light of the first user device 102 to activate and shine, or any combination thereof.

The notification may be viewed and/or heard by the first user 101, who may then proceed to perform the action indicated in the notification. If the first user 101 has not performed the action within a threshold period of time or at a time specified by the first user 101 or the system 100, the system 100 may transmit another alert to the first user device 102 reminding the first user 101 to perform the action. If the user has performed the action specified in the notification, the system 100 may confirm this by obtaining information again from the dental device 110, dispenser 125, toothbrush head 118, or a combination thereof. Based on the additional information, the system 100 may confirm whether the action was successfully completed. If the action is confirmed to be successfully completed, the system 100 may generate a notification indicating successful completion of the action and transmit the notification to the first user device 102. The notification may be outputted via the first user device 102. In certain embodiments, the system 100 may cause the dental device 110, the dispenser 125, and/or the toothbrush head 118 to transmit notifications or alerts to the first user device 102 reminding the first user 101 of an upcoming dentist appointment, reminding the first user 101 when he has to brush his teeth next, reminding the first user 101 to recharge the dental device 110, reminding the first user 101 to refill the container 126 of the dispenser 125, reminding the first user 101 to use the dispenser 125 while using the dental device 110, reminding the first user 101 to use dental floss, reminding the first user 101 to use oral irrigators or other dental devices, reminding the first user 101 to brush each and every tooth, and/or any other notifications. Once the first user 101 is done using the dental device 110, the first user 101 may remove his toothbrush head 118 and allow the second user 105 to attach her toothbrush head 118 to the dental device 110. The system 100 may then track the second user's 105 use of the dental device 110, dispenser 125, and/or the toothbrush head 118 and transmit notifications to the second user device 106 accordingly. Notably, the functionality of the system 100 may incorporate any of the functionality of the method 300 described below and/or any other functionality described herein.

Notably, as shown in FIG. 1, the system 100 may perform any of the operative functions disclosed herein by utilizing the processing capabilities of server 160, the storage capacity of the database 155, or any other component of the system 100 to perform the operative functions disclosed herein. The server 160 may include one or more processors 162 that may be configured to process any of the various functions of the system 100. The processors 162 may be software, hardware, or a combination of hardware and software. Additionally, the server 160 may also include a memory 161, which stores instructions that the processors 162 may execute to perform various operations of the system 100. For example, the server 160 may assist in processing loads handled by the various devices in the system 100, such as, but not limited to, communicatively pairing a dental device 110 with a user device; analyzing identifiers of components of the dental device 110; identifying users associated with the dental device 110 based on analyzing the identifiers; tracking, based on the use of the dental device 110, information associated with the users and the dental device 110; determining actions to be performed with the dental device 110; generating notifications indicating the actions to be performed; transmitting the notifications to the user device; determining if the action has been performed; transmitting reminders to perform the action; transmitting notifications indicating successful completion of the action; providing status information for the dental device 110 (or other devices in the system 100); setting appointments with dental professionals; and performing any other suitable operations conducted in the system 100 or otherwise. In one embodiment, multiple servers 160 may be utilized to process the functions of the system 100. The server 160 and other devices in the system 100 may utilize the database 155 for storing data about the devices in the system 100 or any other information that is associated with the system 100. In one embodiment, multiple databases 155 may be utilized to store data in the system 100.

Although FIG. 1 illustrates a specific example configuration of the various components of the system 100 the system 100 may include any configuration of the components, which may include using a greater or lesser number of the components. For example, the system 100 is illustratively shown as including a first user device 102, a second user device 106, a dental device 110, a toothbrush head 118, a dispenser 125, a container 126, a communications network 135, a cell site 137, a server 140, a server 145, a server 160, and a database 155. However, the system 100 may include multiple first user devices 102, multiple second user devices 106, multiple dental devices 110, multiple toothbrush heads 118, multiple dispensers 125, multiple containers 126, multiple communications networks 135, multiple cell sites 137, multiple servers 140, multiple servers 145, multiple servers 160, and multiple databases 155, or any number of any of the other components in the system 100. Furthermore, in certain embodiments, substantial portions of the functionality and operations of the system 100 may be performed by other networks and systems that may be connected to system 100.

Figure 3:
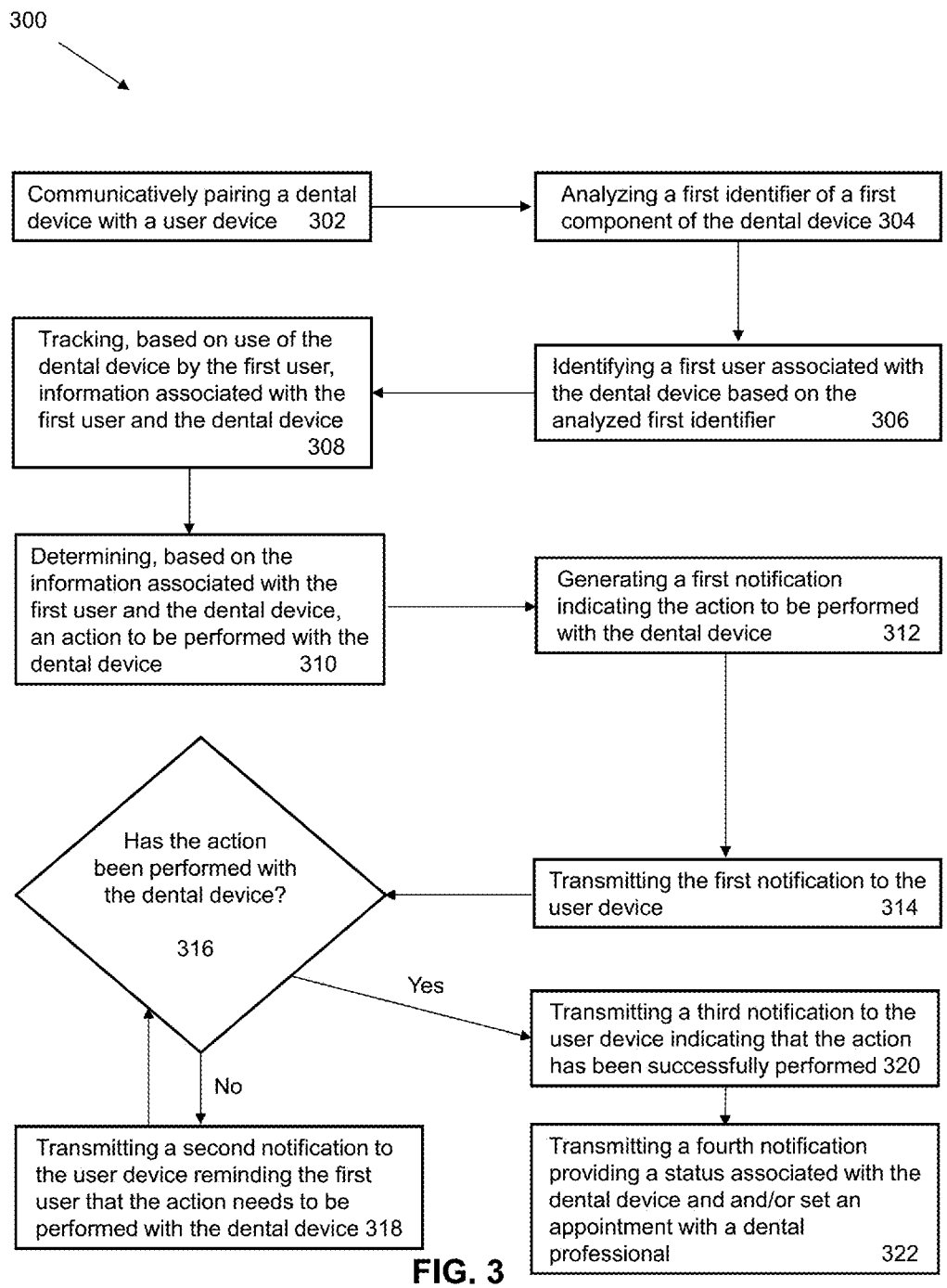
FIG. 3 is a flow diagram illustrating a sample method for providing a connected dental device according to an embodiment of the present disclosure.

As shown in FIG. 3, an exemplary method 300 for providing a connected dental device 110 is schematically illustrated, and may include, at step 302, communicatively pairing a dental device 110 with a user device of a first user 101. For example, the first user 101 may activate short-range wireless functionality on the first user device 102 and communicatively pair the first user device 102 with the dental device 110. The first user device 102 may also be paired with the dispenser 125 or any other device in the system 100. In certain embodiments, the pairing of the dental device 110 with the user device may be performed by or facilitated by utilizing the first user device 102, the second user device 106, the dental device 110, the dispenser 125, the cell site 137, the server 140, the server 145, the server 160, the communications network 135, any combination thereof, or by utilizing any other appropriate program, network, system, or device. At step 304, the method 300 may include analyzing a first identifier of a first component of the dental device 110. For example, using the above scenario, the first component may be the toothbrush head 118 of the dental device 110, and the first identifier may be stored in the communications tag 119 of the toothbrush head 118. The first identifier may be utilized to identify the first user 101 by name, by a unique code, or by other means. In certain embodiments, the analyzing of the first identifier may be performed by utilizing the first user device 102, the second user device 106, the dental device 110, cell site 137, the server 140, the server 145, the server 160, the communications network 135, any combination thereof, or by utilizing any other appropriate program, network, system, or device.

At step 306, method 300 may include identifying the first user 101 of the dental device 110 based on the analyzed first identifier. In certain embodiments, the identifying of the first user 101 may be performed by utilizing the first user device 102, the second user device 106, the dental device 110, cell site 137, the dispenser 125, the server 140, the server 145, the server 160, the communications network 135, any combination thereof, or by utilizing any other appropriate program, network, system, or device. At step 308, the method 300 may include tracking, based on the use of the dental device 110 by the first user 101, information associated with the first user 101 and the dental device 110. For example, the information that may be tracked may include the information stored in the communications tag 119 of the toothbrush head 118, the information stored on the dental device 110, any information obtained from any of the sensors of the dental device 110 and/or toothbrush head 118 (e.g. blood sugar levels, pH levels, temperature measurements, etc.), any calculations performed by the dental device 110, any information obtained from the dispenser 125, any media content from the cameras 122, 124, any other information, or any combination thereof. As another example, the information that may be tracked may include the angle at which the first user 101 holds the dental device 110 while using the dental device 110, the pressure at which the first user 101 holds the toothbrush head 118 against his teeth, the duration of time that the first user 101 uses the dental device 110, the times of day that the first user 101 activates and/or uses the dental device 110, how often the first user 101 uses the dispenser 125 to dispense toothpaste or other cleaning agents, any other information, power levels of the dental device 110 and/or the dispenser 125, or a combination thereof. In certain embodiments, the tracking may be performed by utilizing the first user device 102, the second user device 106, the dental device 110, the dispenser 125, cell site 137, the server 140, the server 145, the server 160, the communications network 135, any combination thereof, or by utilizing any other appropriate program, network, system, or device.

At step 310, the method 300 may include determining, based on the information associated with the first user 101 and the dental device 110, an action to be performed with the dental device 110, by the first user 101, with the dispenser 125, and/or otherwise. For example, based on analyzing the tracked information, the analyzed tracked information may indicate that the first user 101 did not brush several teeth on the left side of the first user's 101 jaw while the first user 101 brushed his teeth. As another example, the tracked information may indicate that the charge remaining in the power source 116 has fallen below a threshold level since or while the first user 101 used the dental device 110 to brush his teeth. In certain embodiments, the determining may be performed by utilizing the first user device 102, the second user device 106, the dental device 110, the dispenser 125, cell site 137, the server 140, the server 145, the server 160, the communications network 135, any combination thereof, or by utilizing any other appropriate program, network, system, or device. At step 312, the method 300 may include generating a first notification or a first reminder that indicates the determined action to be performed. In certain embodiments, the generation of the first notification may be performed by utilizing the first user device 102, the second user device 106, the dental device 110, the dispenser 125, cell site 137, the server 140, the server 145, the server 160, the communications network 135, any combination thereof, or by utilizing any other appropriate program, network, system, or device. At step 314, the method 300 may include transmitting the first notification to the user device. For example, the dental device 110 may transmit the generated notification to the first user device 102 for display on a user interface of an application of the first user device 102. In certain embodiments, the transmitting may be performed by utilizing the first user device 102, the second user device 106, the dental device 110, the dispenser 125, cell site 137, the server 140, the server 145, the server 160, the communications network 135, any combination thereof, or by utilizing any other appropriate program, network, system, or device.

At step 316, the method 300 may include determining if the action identified in the notification has been performed. For example, if the notification indicated that the first user 101 needs to recharge the power source 116 of the dental device, the system 100 may determine if the first user 101 has recharged the power source 116, such as to a threshold level. As another example, if the notification indicated that the first user 101 needed to brush several teeth on the left side of the first user's 101 mouth, the system 100 may determine by analyzing additional information obtained from the sensors, cameras 122, 124, and/or other componentry of the dental device 110 whether the first user 101 brushed the teeth on the left side of the first user's 101 mouth. In certain embodiments, the determining may be performed by utilizing the first user device 102, the second user device 106, the dental device 110, the dispenser 125, cell site 137, the server 140, the server 145, the server 160, the communications network 135, any combination thereof, or by utilizing any other appropriate program, network, system, or device. If, at step 316, it is determined that the first user 101 has not performed the action identified in the first notification, the method 300 may include generating and transmitting a second notification or second reminder to the first user device 102. The second notification may remind the first user 101 that the first user 101 needs to perform the action. In certain embodiments, the generating and transmitting may be performed by utilizing the first user device 102, the second user device 106, the dental device 110, the dispenser 125, cell site 137, the server 140, the server 145, the server 160, the communications network 135, any combination thereof, or by utilizing any other appropriate program, network, system, or device.

If, however, at step 316, it is determined that the first user 101 has performed the action identified in the notification, the method 300 may include proceeding to step 320, which may include transmitting a third notification to the first user device 102 indicating that the action has been successfully performed. For example, using the above example, if the first user 101 brushed the teeth on the left side of his mouth, the system 100 may generate a notification indicating successful completion of the brushing of his teeth and transmit the notification to the first user device 102. In certain embodiments, the generating and transmitting of the third notification may be performed by utilizing the first user device 102, the second user device 106, the dental device 110, the dispenser 125, cell site 137, the server 140, the server 145, the server 160, the communications network 135, any combination thereof, or by utilizing any other appropriate program, network, system, or device. At step 322, the method 300 may include generating and transmitting a fourth notification that may provide a status associated with the dental device 110, the dispenser 125, or any other device in the system 100. For example, the fourth notification may indicate a power level of the dental device 110, whether the dental device 110 is in use or not in use, information collected from the sensors of the dental device 110 and/or toothbrush head 118, information indicating the amount of days until the first user's 102 next dental appointment, information indicating a usage pattern associated with how the first user 101 uses the dental device 110, information summarizing the brushing style the first user 101 uses when using the dental device 110, information identifying how much toothpaste or cleaning agents were dispensed from the dispenser 125, whether any cavities were detected, whether any gum disease was detected, any media content obtained by the cameras 122, 124, any other information or content, or a combination thereof. Also, at step 322, the method 300 may include setting an appointment for the first user 101 to visit a dentist and/or providing a reminder for such an appointment. In certain embodiments, the fourth notification and/or the setting of the appointment may be performed by utilizing the first user device 102, the second user device 106, the dental device 110, the dispenser 125, cell site 137, the server 140, the server 145, the server 160, the communications network 135, any combination thereof, or by utilizing any other appropriate program, network, system, or device. Notably, the method 300 may further incorporate any of the functionality and features as described for system 100 or as otherwise described herein.

Notably, the system 100 and methods disclosed herein may include additional functionality and features. For example, in certain embodiments, the system 100 and methods may include enabling the system 100 to determine if the bristles 123 have been worn out beyond a threshold amount based on analyzing the media content from the cameras 122, 124. If the bristles 123 are worn out beyond the threshold amount, the system 100 may transmit a notification to the first user device 102 indicating that the first user 101 has to replace the toothbrush head 118. In certain embodiments, the system 100 and methods may include detecting usage patterns associated with the first user's 101 use of the dental device 110 and/or the dispenser 125. For example, the system 100 may determine that the first user 101 only uses the dental device 110 once a day. In such a scenario, the system 100 may transmit an alert or notification to the first user device 102 indicating that the first user 101 needs to brush his teeth at least twice daily. In certain embodiments, the system 100 and methods may include transmitting notifications to the first user device 102 indicating that the first user 101 needs to adjust the angle at which the first user 101 brushes his teeth, notifications indicating that certain portions of teeth have not been brushed, notifications indicating that the first user's 101 tongue has not been brushed, notifications indicating that the first user 101 has not flossed his teeth, notifications that the first user 101 should reduce his sugar intake based on his detected blood sugar levels, notifications that the first user 101 may have a fever based on the temperature measurements from the temperature sensor 120, notifications indicating that the first user's 101 gum line has receded and that a dental appointment is necessary, notifications indicating the presence of cavities, notifications indicating the presence of broken or chipped teeth, notifications indicating abnormal pH levels, notifications indicating any type of dental condition, or any combination thereof.

In certain embodiments, the system 100 and methods may determine whether the first user 101 or the second user 105 has a dental disease or condition based on comparing the tracked information to previous photos or videos taken of the first or second user's 101, 105 mouth. In certain embodiments, the system 100 and methods may be utilized to determine measure the age of the toothbrush head 118 by counting each time the first user 101 attaches the toothbrush head 118 to the dental device 110. In certain embodiments, the system 100 and methods may be utilized to detect inflammation in gums or in other areas of the first user's 101 mouth. In certain embodiments, the notifications may be displayed on the first and second user devices 102, 106, and, in certain embodiments, the notifications may be displayed or outputted on the dental device 110 itself, such as via the display 131. In certain embodiments, the dental device 110, the toothbrush head 118, and/or the dispenser 125 may each have their own internet protocol addresses, which may be utilized by the communications network 135, servers 140, 145, and the first and second user devices 102, 106 to identify the dental device 110, the toothbrush head 118, and/or dispenser 125 and communicate with them.

In certain embodiments, the notifications may be sent to a display or output device of a connected vehicle, a display or output device of a connected home, to a display or output device of a connected dog collar, or to any other connected device. In certain embodiments, the system 100 and methods may be cause signals to be sent to the dispenser 125 to automatically cause the toothpaste and/or cleaning agents to be dispensed from the dispenser 125 upon receipt of the signals. In certain embodiments, any tracked information may be sent to one or more devices of a dentist taking care of the first user 101. This may allow the dentist to diagnose conditions and/or recommend dental care regimens remotely. Once conditions are diagnosed and/or regimens are made, the dentist may use one of her devices to transmit notifications to the dental device 110, the dispenser 125, and/or the first and second user devices 102, 106 to indicate the diagnosed conditions and/or recommended regimens. In certain embodiments, the system 100 and methods may be utilized to track any number of users.

Figure 4:
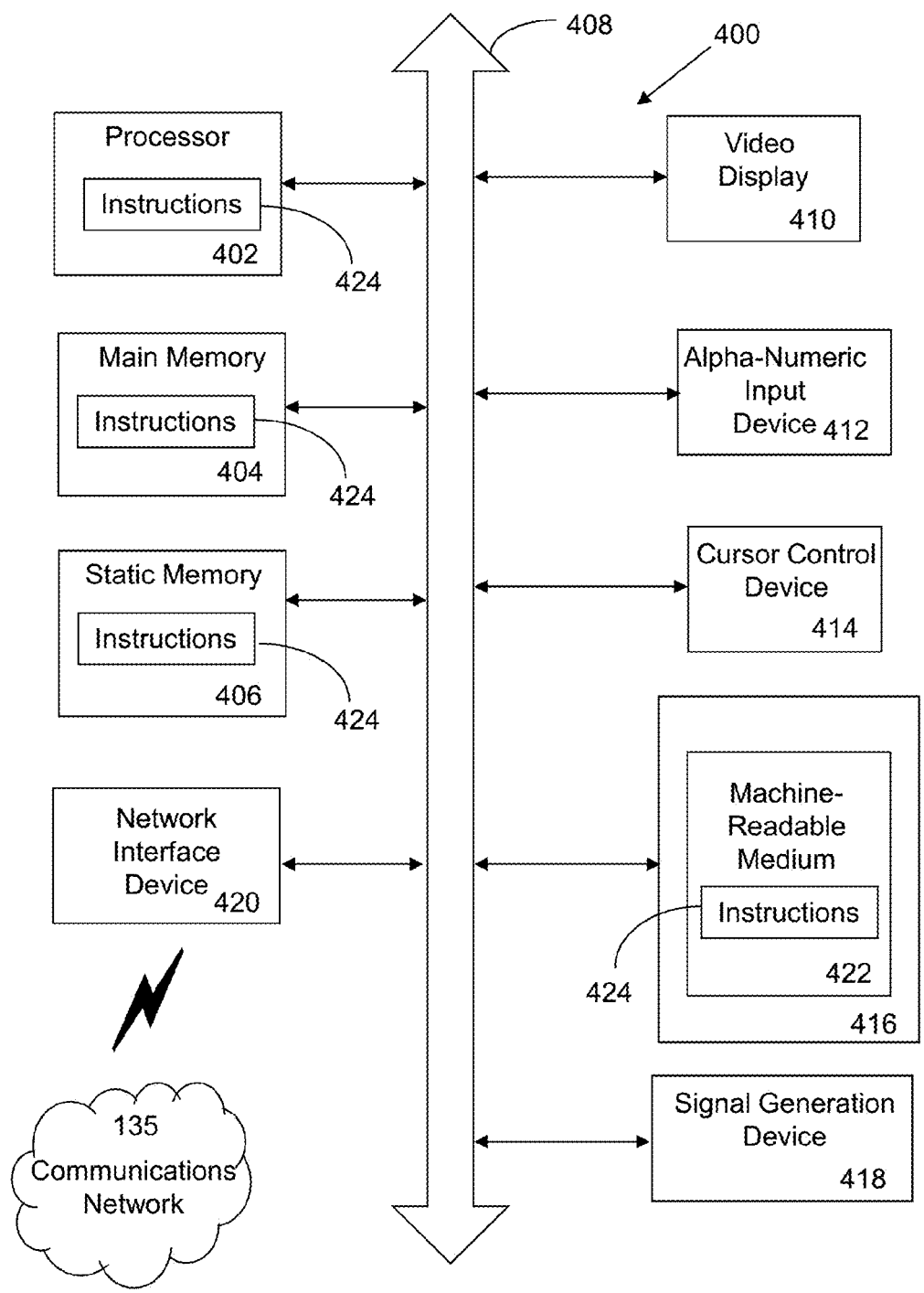
FIG. 4 is a schematic diagram of a machine in the form of a computer system within which a set of instructions, when executed, may cause the machine to perform any one or more of the methodologies or operations of the systems and methods for providing a connected dental device.

Referring now also to FIG. 4, at least a portion of the methodologies and techniques described with respect to the exemplary embodiments of the system 100 can incorporate a machine, such as, but not limited to, computer system 400, or other computing device within which a set of instructions, when executed, may cause the machine to perform any one or more of the methodologies or functions discussed above. The machine may be configured to facilitate various operations conducted by the system 100. For example, the machine may be configured to, but is not limited to, assist the system 100 by providing processing power to assist with processing loads experienced in the system 100, by providing storage capacity for storing instructions or data traversing the system 100, or by assisting with any other operations conducted by or within the system 100.

In some embodiments, the machine may operate as a standalone device. In some embodiments, the machine may be connected (e.g., using communications network 135, another network, or a combination thereof) to and assist with operations performed by other machines and systems, such as, but not limited to, the first user device 102, the second user device 106, the dental device 110, the toothbrush head 118, the dispenser 125, the container 126, the cell site 137, the server 140, the server 145, the database 155, the server 160, or any combination thereof. The machine may be connected with any component in the system 100. In a networked deployment, the machine may operate in the capacity of a server or a client user machine in a server-client user network environment, or as a peer machine in a peer-to-peer (or distributed) network environment. The machine may comprise a server computer, a client user computer, a personal computer (PC), a tablet PC, a laptop computer, a desktop computer, a control system, a network router, switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The computer system 400 may include a processor 402 (e.g., a central processing unit (CPU), a graphics processing unit (GPU, or both), a main memory 404 and a static memory 406, which communicate with each other via a bus 408. The computer system 400 may further include a video display unit 410, which may be, but is not limited to, a liquid crystal display (LCD), a flat panel, a solid state display, or a cathode ray tube (CRT). The computer system 400 may include an input device 412, such as, but not limited to, a keyboard, a cursor control device 414, such as, but not limited to, a mouse, a disk drive unit 416, a signal generation device 418, such as, but not limited to, a speaker or remote control, and a network interface device 420.

The disk drive unit 416 may include a machine-readable medium 422 on which is stored one or more sets of instructions 424, such as, but not limited to, software embodying any one or more of the methodologies or functions described herein, including those methods illustrated above. The instructions 424 may also reside, completely or at least partially, within the main memory 404, the static memory 406, or within the processor 402, or a combination thereof, during execution thereof by the computer system 400. The main memory 404 and the processor 402 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine-readable medium 422 containing instructions 424 so that a device connected to the communications network 135, another network, or a combination thereof, can send or receive voice, video or data, and to communicate over the communications network 135, another network, or a combination thereof, using the instructions. The instructions 424 may further be transmitted or received over the communications network 135, another network, or a combination thereof, via the network interface device 420.

While the machine-readable medium 422 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that causes the machine to perform any one or more of the methodologies of the present disclosure.

The terms "machine-readable medium," "machine-readable device, or "computer-readable device" shall accordingly be taken to include, but not be limited to: memory devices, solid-state memories such as a memory card or other package that houses one or more read-only (non-volatile) memories, random access memories, or other re-writable (volatile) memories; magneto-optical or optical medium such as a disk or tape; or other self-contained information archive or set of archives is considered a distribution medium equivalent to a tangible storage medium. The "machine-readable medium," "machine-readable device," or "computer-readable device" may be non-transitory, and, in certain embodiments, may not include a wave or signal per se. Accordingly, the disclosure is considered to include any one or more of a machine-readable medium or a distribution medium, as listed herein and including art-recognized equivalents and successor media, in which the software implementations herein are stored.

The illustrations of arrangements described herein are intended to provide a general understanding of the structure of various embodiments, and they are not intended to serve as a complete description of all the elements and features of apparatus and systems that might make use of the structures described herein. Other arrangements may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Thus, although specific arrangements have been illustrated and described herein, it should be appreciated that any arrangement calculated to achieve the same purpose may be substituted for the specific arrangement shown. This disclosure is intended to cover any and all adaptations or variations of various embodiments and arrangements of the invention. Combinations of the above arrangements, and other arrangements not specifically described herein, will be apparent to those of skill in the art upon reviewing the above description. Therefore, it is intended that the disclosure not be limited to the particular arrangement(s) disclosed as the best mode contemplated for carrying out this invention, but that the invention will include all embodiments and arrangements falling within the scope of the appended claims.

The foregoing is provided for purposes of illustrating, explaining, and describing embodiments of this invention. Modifications and adaptations to these embodiments will be apparent to those skilled in the art and may be made without departing from the scope or spirit of this invention. Upon reviewing the aforementioned embodiments, it would be evident to an artisan with ordinary skill in the art that said embodiments can be modified, reduced, or enhanced without departing from the scope and spirit of the claims described below.

We claim:

1. A dental device, comprising:
a memory that stores instructions; and
a processor that executes the instructions to perform operations, the operations comprising:
  monitoring, based on use of the dental device by a first user, first information associated with the first user and the dental device, wherein the first information associated with the first user and the dental device is obtained from a sensor of the dental device;
  detecting a dental condition of the first user by comparing visual content of the first user obtained by the dental device during use of the dental device to previous visual content obtained during a prior use of the dental device;
  determining, based on the first information associated with the first user and the dental device, an action to be performed by the first user with the dental device;
  transmitting, to a user device of the first user, a first notification indicating the action to be performed with the dental device;
  determining, based on second information associated with the first user and the dental device obtained from the sensor, if the action has been performed with the dental device; and
  transmitting, if the action has been performed, a second notification to the user device of the first user indicating successful completion of the action.

2. The dental device of claim 1, wherein the operations further comprise transmitting, if the action has not been performed, a third notification to the user device reminding the first user to perform the action with the dental device.

3. The dental device of claim 1, wherein the operations further comprise generating an appointment for the first user.

4. The dental device of claim 1, wherein the operations further comprise determining if a component of the dental device needs to be replaced.

5. The dental device of claim 1, wherein the operations further comprise detecting a usage pattern associated with use of the dental device by the first user.

6. The dental device of claim 5, wherein the operations further comprise determining, based on the usage pattern, a new action to be performed by the first user with the dental device.

7. The dental device of claim 6, wherein the operations further comprise transmitting a third notification to the user device indicating the new action to be performed by the first user with the dental device.

8. The dental device of claim 1, wherein the operations further comprise detecting a dental condition of the first user based on the first information associated with the first user and the dental device obtained from the sensor.

9. The dental device of claim 1, wherein the operations further comprise obtaining, from a camera of the dental device, media content of the first user while the first user is utilizing the dental device.

10. The dental device of claim 1, wherein the operations further comprise monitoring a power level of the dental device, and wherein the operations further comprise transmitting, if the power level is below a threshold, an alert to the user device indicating that the dental device needs to be recharged.

11. The dental device of claim 1, wherein the operations further comprise identifying the first user based on an identifier of a component of the dental device.

12. The dental device of claim 1, wherein the operations further comprise transmitting a signal to a dispenser communicatively linked to the dental device to dispense a solution onto the dental device.

13. The dental device of claim 1, wherein the operations further comprise determining a bruServalg technique utilized by the first user based on the first information associated with the first user and the dental device obtained from the sensor.

14. A method, comprising:
monitoring, based on use of a dental device by a first user, first information associated with the first user and the dental device, wherein the first information associated with the first user and the dental device is obtained from a sensor of the dental device;
determining, based on the first information associated with the first user and the dental device, an action to be performed by the first user with the dental device, wherein the determining is performed by utilizing instructions from a memory that are executed by a processor, wherein the first information includes information indicating times when the dental device is activated by the first user;
detecting a dental condition of the first user by comparing visual content of the first user obtained by the dental device during use of the dental device to previous visual content obtained during a prior use of the dental device;
transmitting, to a user device of the first user, a first notification indicating the action to be performed with the dental device;
determining, based on second information associated with the first user and the dental device obtained from the sensor, if the action has been performed with the dental device; and
transmitting, if the action has not been performed, a second notification to the user device of the first user reminding the first user to perform the action.

15. The method of claim 14, further comprising determining, based on the first information associated with the first user and the dental device, a pressure at which the first user holds a component of the dental device against teeth of the first user.

16. The method of claim 14, further comprising determining, based on the first information associated with the first user and the dental device, a duration of time that the first user utilized the dental device.

17. The method of claim 14, further comprising determining, based on the first information associated with the first user and the dental device, a brushing speed associated with the dental device.

18. The method of claim 14, further comprising determining a blood sugar level of the first user based on the first information associated with the first user and the dental device.

19. The method of claim 14, further comprising determining a temperature of the first user based on the first information associated with the first user and the dental device.

20. A non-transitory computer-readable device comprising instructions, which when executed by a processor, cause the processor to perform operations comprising:

analyzing, based on use of the dental device by a first user, first information associated with the first user and the dental device, wherein the first information associated with the first user and the dental device is obtained from a sensor of the dental device, wherein the first information includes information indicating times when the dental device is activated by the first user;

detecting a dental condition of the first user by comparing visual content of the first user obtained by the dental device during use of the dental device to previous visual content obtained during a prior use of the dental device;

determining, based on the first information associated with the first user and the dental device, an action to be performed by the first user with the dental device;

providing, to a user device of the first user, a first notification indicating the action to be performed with the dental device;

determining, based on second information associated with the first user and the dental device obtained from the sensor, if the action has been performed with the dental device; and providing, if the action has been performed, a second notification to the user device of the first user indicating successful completion of the action.

\* \* \* \* \*